United States Patent
Trousset et al.

(10) Patent No.: US 10,163,205 B2
(45) Date of Patent: Dec. 25, 2018

(54) THREE DIMENSIONAL IMAGING METHOD OF A LIMITED ZONE OF A PATIENT'S VASCULATURE

(71) Applicant: GENERAL ELECTRIC COMPANY, Schenectady, NY (US)

(72) Inventors: Yves Lucien Trousset, Buc (FR); Cyril Riddell, Buc (FR); Vincent Jonas Bismuth, Buc (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/109,346

(22) PCT Filed: Dec. 31, 2013

(86) PCT No.: PCT/IB2013/002985
§ 371 (c)(1),
(2) Date: Jun. 30, 2016

(87) PCT Pub. No.: WO2015/101797
PCT Pub. Date: Jul. 9, 2015

(65) Prior Publication Data
US 2016/0328846 A1    Nov. 10, 2016

(51) Int. Cl.
G06K 9/00 (2006.01)
G06T 7/00 (2017.01)
G06T 19/00 (2011.01)
A61B 5/00 (2006.01)
G06F 3/0484 (2013.01)
(Continued)

(52) U.S. Cl.
CPC ............ *G06T 7/0012* (2013.01); *A61B 5/489* (2013.01); *A61B 6/481* (2013.01); *A61B 6/504* (2013.01); *G06F 3/04842* (2013.01); *G06T 19/003* (2013.01); *A61B 6/032* (2013.01); *A61B 6/466* (2013.01); *A61B 6/486* (2013.01); *A61B 6/5211* (2013.01); *G06T 2200/24* (2013.01)

(58) Field of Classification Search
None
See application file for complete search history.

(56) References Cited

U.S. PATENT DOCUMENTS 6,690,816 B2    2/2004  Aylward et al.
6,711,433 B1 *  3/2004  Geiger .................. A61B 6/463
                                                      378/42
(Continued)

FOREIGN PATENT DOCUMENTS

WO    2006085288 A2    8/2006

OTHER PUBLICATIONS

International Search Report and Written Opinion for PCT/IB2013/002985, dated Jan. 27, 2015, 23 pages.
(Continued)

*Primary Examiner* — Randolph I Chu
(74) *Attorney, Agent, or Firm* — GE Global Patent Operation; Marc A. Vivenzio

(57) ABSTRACT

This disclosure relates to a three dimensional visualization method for visualizing and/or displaying a limited zone of a patient's vasculature, the method comprising selecting an entry point within an imaged vasculature and three dimensionally visualizing a simulated contrast agent propagation from the selected entry point in a limited zone of the imaged vasculature.

16 Claims, 1 Drawing Sheet

(51) Int. Cl.
*A61B 6/03* (2006.01)
*A61B 6/00* (2006.01)

(56) References Cited

U.S. PATENT DOCUMENTS

| | | | | |
|---|---|---|---|---|
| 2008/0020362 A1* | 1/2008 | Cotin | ............... | G16H 50/50 434/267 |
| 2009/0270790 A1* | 10/2009 | Raghavan | ............ | A61M 37/00 604/22 |
| 2010/0172567 A1* | 7/2010 | Prokoski | ............ | A61B 5/0064 382/132 |
| 2012/0201439 A1* | 8/2012 | Rauch | ............... | G06T 7/20 382/130 |
| 2014/0094680 A1* | 4/2014 | Kowarschik | ............ | A61B 6/507 600/407 |
| 2014/0162016 A1* | 6/2014 | Matsui | ............... | B29C 69/00 428/76 |

OTHER PUBLICATIONS

Schmitt et al., Reconstruction of blood propagation in three-dimensional rotational X-ray angiography (3D-RA), Computerized Medical Imaging and Graphics, vol. 29, No. 7, Oct. 1, 2005, 14 pages.
Schmitt et al., An X-Ray-Based Method for the Determination of the Contrast Agent Propagation in 3-D Vessel Structures, IEEE Transactions on Medical Imaging, vol. 21, No. 3, Mar. 1, 2002, 12 pages.

* cited by examiner

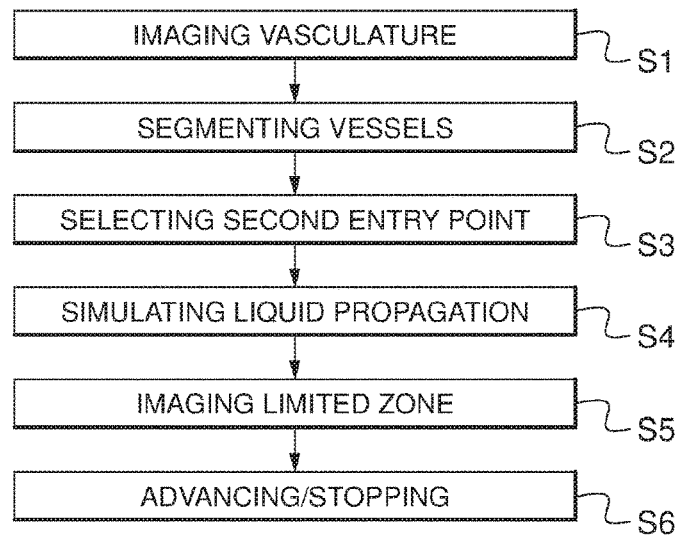
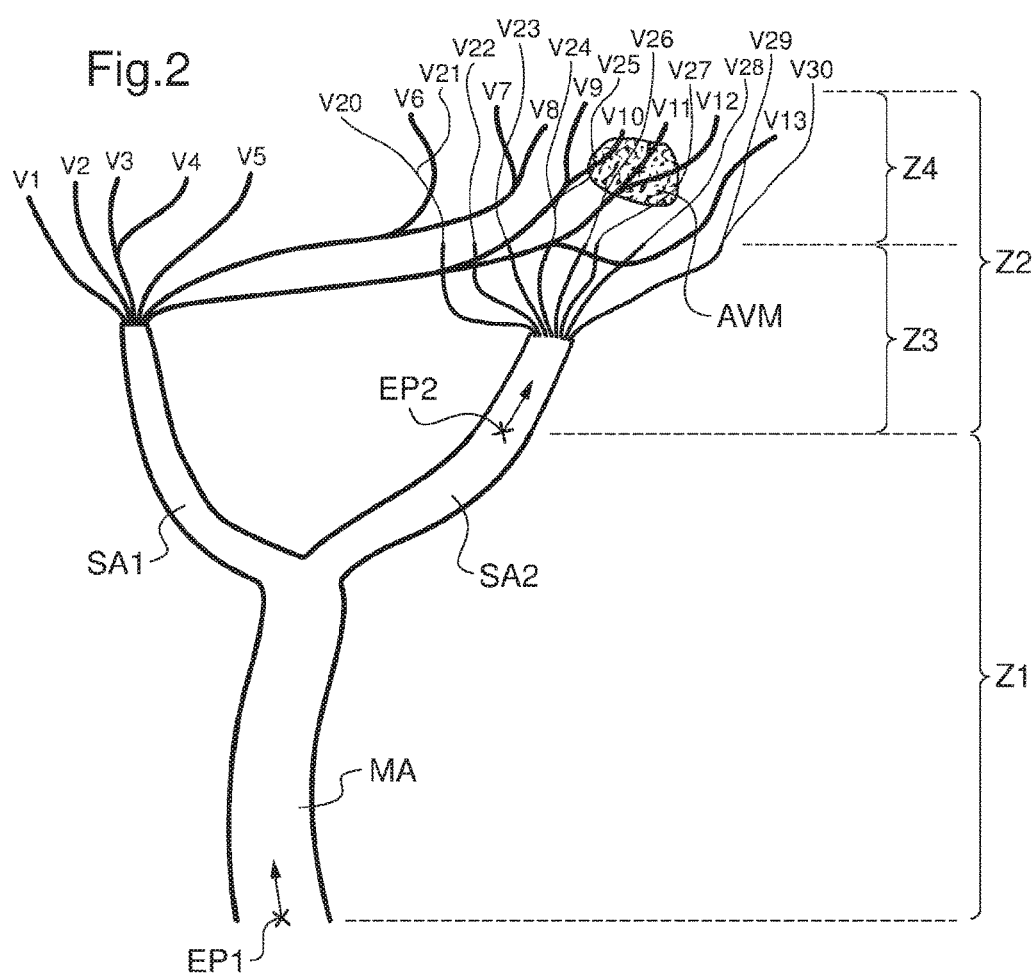

ize the patient's vasculature in the three dimensional image. Therefore, embodiments of the invention aim to ease the visualization of three dimensional images of patient's vasculature. Preferably, a new dimension, which is the time dimension, is brought in the representation of an image which is already a static three dimensional image. The resulting three dimensional image plus time (3D+t) information, avoids vessel superimposition and eases the visual tracking of a vascular path in the three dimensional image where many vessels may be entangled. This type of proposed representation will ease the understanding of the vascular architecture, it will ease the navigation of a tool (e.g. guidewire, catheter) within this vascular architecture and it will also ease the identification of the feeder(s) of the targeted pathology (tumor or arteriovenous malformation).
THREE DIMENSIONAL IMAGING METHOD OF A LIMITED ZONE OF A PATIENT'S VASCULATURE

CROSS-REFERENCE TO RELATED APPLICATIONS

This application is a US PCT National Phase filing under 35 U.S.C. 371 of copending International Application No. PCT/IB2013/002985, filed Dec. 31, 2013, which is incorporated herein by reference in its entirety.

TECHNICAL FIELD

The disclosure relates to three dimensional imaging methods of human vasculature.

BACKGROUND OF THE INVENTION

When imaging a patient's vasculature and when trying to isolate a limited zone of this patient's vasculature, when zooming in a limited zone of this patient's vasculature, what happens is that many vessels are entangled in this limited zone. Therefore, it may not be easy for the radiologist to build in his mind a clear representation of the vasculature architecture in this limited zone or a region of specific interest, including vessel bifurcations or an arteriovenous malformation.

When performing an intervention, the radiologist navigates a tool through the network of vessels with the help of two-dimensional projective images. Vessels may not be visible if no contrast is injected. State-of-the-art interventional systems superimpose over these projective images a two dimensional rendering of the vessel configuration obtained from a prior three dimensional image of the vessels in order to avoid multiple local contrast injections that would image the local configuration of the vessels where the tool is navigated. However, the number of vessels in the three dimensional image and their possible superimposition in the projective images can make difficult the interpretation of the actual local vessel configuration and suggest routes that the tool cannot actually take. Anatomical variations that naturally arise in the population make possible unexpected ambiguous interpretation of the two dimensional rendering.

Similarly, the number of small vessels and their possible relative superimposition in the three dimensional image can make the three dimensional interpretation of a pathology complex. This is particularly the case during the treatment of an arteriovenous malformation. The radiologist would like to identify the vessel(s) which feed(s) the core of the malformation. To try to make this identification, the radiologist visually follows the vessel leading to the pathology using volume rendered two-dimensional views of the volumetric image which are available on the visualization workstation. Each time the feeder, which means the feeding blood vessel, is superimposed to another vessel, the analysis becomes more ambiguous.

The visualization of complex vascular structures in a three dimensional image is a challenging task for the interventional radiologist. Moreover, for an arteriovenous malformation (AVM) treatment, this is even more challenging because the anatomy of such malformations is indeed a complex pattern of abnormally entangled vessels. This is also the case, although to a lesser degree, when analyzing a tumor that has grown a new vessel system to feed itself, as such abnormal vessels are also characteristically disorderly entangled over a feeder vessel that is thus hard to identify.

According to a first prior art, it is known, for radiologists, to use oblique planar representation of the three dimensional image to avoid ambiguities. They may have to go through many oblique planes to follow the vessels on all their respective paths.

According to a second prior art, for example described in U.S. Pat. No. 6,690,816, it is known to make a model of blood propagation in a patient's vasculature. However, this model of blood propagation does not improve in any way the visualization of vascular paths, so it is useless to improve patient's vasculature visualization.

SUMMARY OF THE INVENTION

The object of the present invention is to alleviate at least partly the above mentioned drawbacks.

More particularly, the invention aims to improve the visualization of the vascular paths in a limited zone of interest in a patient's vasculature. Therefore, embodiments of the invention aim to separate the vascular paths of interest from alternative vascular paths presenting no specific interest which may be superimposed and entangled with them. Preferably, in a first embodiment, the invention aims to visualize the possible vascular paths as seen from a tool tip position without visualizing neighboring vessels that are not connected to the tool tip position but that would be superimposed to the vessels of interest in a standard rendering view; in a second embodiment the invention aims to visualize the feeding vessel(s) of a pathology (tumor or arteriovenous malformation) without visualizing simultaneously the neighboring vessels which do not feed this pathology.

To facilitate the analysis of the vascular architecture, embodiments of the invention propose new ways to visualize the patient's vasculature in the three dimensional image. Therefore, embodiments of the invention aim to ease the visualization of three dimensional images of patient's vasculature. Preferably, a new dimension, which is the time dimension, is brought in the representation of an image which is already a static three dimensional image. The resulting three dimensional image plus time (3D+t) information, avoids vessel superimposition and eases the visual tracking of a vascular path in the three dimensional image where many vessels may be entangled. This type of proposed representation will ease the understanding of the vascular architecture, it will ease the navigation of a tool (e.g. guidewire, catheter) within this vascular architecture and it will also ease the identification of the feeder(s) of the targeted pathology (tumor or arteriovenous malformation).

This object is achieved with a three dimensional imaging method of a limited zone of a patient's vasculature, comprising: three dimensional imaging of the map of the propagation of a real contrast agent, from a first entry point, in at least part of said vasculature, selecting a second entry point, different from said first entry point, within said imaged vasculature, three dimensional imaging of a simulated contrast agent propagation, from selected second entry point, in a limited zone of said imaged vasculature. This limited zone of said imaged vasculature is of course included within the imaged vasculature itself.

This object is also achieved with an interventional imaging system, wherein it is: adapted to three dimensionally image the map of a real contrast agent propagation, from a first entry point, in at least part of a patient's vasculature, adapted to allow selection, by user, of a second entry point, different from said first entry point, within said imaged vasculature, adapted to three dimensionally image a simulated contrast agent propagation, from selected second entry point, in a limited zone of said imaged vasculature.

This object is also achieved by a three dimensional visualization method which uses an already existing three dimensional image of vasculature. This object is also achieved by a three dimensional visualization method which uses an already existing imaged vasculature, whatever the way this vasculature has been imaged. So, this object is also achieved by a three dimensional visualization method of a limited zone of a patient's vasculature, comprising selecting an entry point within an imaged vasculature, three dimensional visualization of a simulated contrast agent propagation, from selected entry point, in a limited zone of said imaged vasculature. And this object is also achieved by a three dimensional visualization method of a limited zone of a patient's vasculature, comprising selecting an imaged vasculature obtained from a three dimensional imaging of at least part of a vasculature in which there was a real contrast agent propagation starting from a first entry point, selecting a second entry point, within said imaged vasculature, second entry point being different from said first entry point, three dimensional visualization of a simulated contrast agent propagation, from selected second entry point, in a limited zone of said imaged vasculature.

Preferred embodiments comprise one or more of the following features, which can be taken separately or together, either in partial combination or in full combination.

Preferably, the three dimensional imaging method also comprises segmenting visible vessels of said imaged vasculature, said second entry point is selected along one of said segmented visible vessels, and said imaged limited zone only comprises some of said segmented visible vessels. The segmentation of visible vessels in the imaged vasculature is very helpful to build the three dimensional network of the blood vessels which will afterwards be used to simulate the contrast or blood propagation within at least part of this three dimensional map of the blood vessels.

Preferably, the three dimensional imaging method is performed by an interventional imaging system. Intrinsic flexibility of interventional imaging system and flexibility of proposed three dimensional imaging method according to embodiments of the invention combine together to offer a very flexible system allowing for visualizing the zone of interest in patient's vasculature, all this zone and only this zone, so getting rid of other portions of vasculature that are not of peculiar interest but which are mixed with the zone of interest of patient's vasculature on the displayed image.

Said limited zone may comprise at least some of said segmented visible vessels with some tortuosity so that it is not easy to understand which routes are possible from the tool tip from practical two dimensional viewpoints, thereby making all the more interesting the three dimensional imaging method according to embodiments of the invention. Embodiments of the invention are specifically interested in being able to select the vessels a tool can enter from a given position of the tool tip, from the rest of vessels of the vasculature which, without this separation, would be superimposed and could be confusingly interpreted as potential directions.

Preferably, said limited zone comprises at least some of said segmented visible vessels feeding an arteriovenous malformation or a tumor. Embodiments of the invention are specifically interested in an arteriovenous malformation or a tumor, and in being able to separate the feeding blood vessels of this arteriovenous malformation or tumor from the rest of vessels of the vasculature which, without this separation, would be entangled with those feeding blood vessels.

Preferably, in a first option, said three dimensional imaging of said simulated contrast agent propagation is a static graphic representation (map) of said segmented visible vessels of said imaged limited zone completed with a static representation code, preferably a color code, as a function of propagation time from said second entry point. This static representation, which will be discussed in more detail with respect to FIG. 2, is a simple way to visualize the vascular paths of interest.

Preferably, in a second option, said three dimensional imaging of said simulated contrast agent propagation is a cinematic representation of said segmented visible vessels of said imaged limited zone, showing directly the propagation, from said second entry point, as a function of propagation time, of contrast along said segmented visible vessels of said limited zone. This cinematic representation, which is more sophisticated, allows for a clearer way to visualize the vascular paths of interest.

Preferably, said simulated cinematic contrast agent propagation can be stopped, rewinded, advanced or looped through, by user, so as to graphically represent a vascular path of at least a segmented visible vessel of said limited zone with a varying degree of complexity. This option in the imaging treatment is very useful, since it helps the radiologist to visually follow the vascular path of interest more easily and plan the insertion of a therapeutic tool accordingly.

Preferably, said first entry point is the entry point of main artery of said vasculature. That way, all vasculature can then be imaged, and afterwards the radiologist will be able to simulate contrast propagation in any limited zone of said imaged vasculature.

Preferably, each said segmented visible vessel is represented by only two parameters, its centerline and its diameter. Indeed, what is needed here is simply a clear representation of the vascular paths of interest, so that for instance the feeding vessels of an arteriovenous malformation or a tumor can be identified easily. A sophisticated and more realistic representation of the vessels architecture and of the blood propagation along them, even if it may be useful, is not compulsory. Therefore, a very simple way of representing blood vessels is preferably chosen.

Preferably, said contrast agent propagation is simulated by progressively filling said segmented visible vessels of said limited zone up to a geodesic distance $d=v*t$ from said second entry point, with v a constant velocity and t the propagation time. Here, again, a very simple way of representing the contrast propagation within the vessels of the limited zone of patient's vasculature, will be considered to be sufficient for the radiologist. The very simple representation of contrast propagation within vessels is by the way rather cheap and easy to implement.

Preferably, said contrast agent propagation is simulated for a limited amount of contrast by progressively filling said segmented visible vessels of said limited zone up to a geodesic distance of $d=v*t$ from said second entry point, with v a constant velocity, with t the propagation time, and with contrast concentration $c(d)$ either constant or inversely proportional to d, so that the dilution of the contrast as it propagates within the blood stream is also simulated in order to preferentially highlight the vessels in the vicinity of the entry point set. When navigating a tool, the second entry point is preferably set at the tool tip, which may be done by the user or obtained automatically from the device monitoring the tool, such as the projective two dimensional X-ray images of the tool or coordinates form an electromagnetic tool tracking system.

Preferably, said three dimensional imaging of real contrast agent propagation, from said first entry point, is computed from several, preferably more than 100, two dimensional images each including real contrast agent propagation information.

Preferably, segmented visible vessels of said limited zone include vessels which diameter is less than 1 mm. This means that the limited zone of patient's vasculature which can be visualized may include portions of vasculature constituted of quite small vessels which usually may not even be visible in acquired projective images of patient's vasculature, but hidden by superimposed vessels. That way, an arteriovenous malformation in vasculature portions constituted of quite small vessels can be visualized too.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 1 shows an example of the steps of a three dimensional imaging method of a limited zone of a patient's vasculature, performed according to embodiments of the invention.

FIG. 2 shows schematically an example of a patient's vasculature image visualized by a three dimensional imaging method according to embodiments of the invention.

DETAILED DESCRIPTION OF THE INVENTION

FIG. 1 shows an example of the steps of a three dimensional imaging method of a limited zone of a patient vasculature, performed according to embodiments of the invention. Successively performed steps include a step S1 of imaging vasculature, a step S2 of segmenting vessels, a step S3 of selecting a second entry point, a step S4 of simulating a contrast propagation, a step S5 of visualizing a limited zone, and a step S6 of advancing, rewinding, stopping or looping through. These steps S1 to S6 are successively performed by an interventional imaging system. Steps S1 to S6 can also be considered as functional blocks of an interventional imaging system adapted to perform those steps.

In step S1 of imaging vasculature, three dimensional imaging of real contrast agent propagation, from a first entry point, in at least part of said vasculature, is made. First entry point is preferably the entry point of the main artery. Before step S1 is performed, a contrast agent has been injected in patient's artery so that it could propagate through patient's vasculature. The three dimensional imaging of real contrast agent propagation paths, from said first entry point, is computed from several, preferably more than 100, for example about 150, two dimensional images each having real contrast agent propagation path information. The vessels are thus defined by these propagation paths.

In step S2 of segmenting vessels, visible vessels of said imaged vasculature are segmented. This means the vessels are identified from their neighborhood, and are labeled as blood vessels, so that the coordinates of the vascular paths are stored and so that the ramifications of the vessels map may be visualized. Once the vasculature of the patient has been segmented, it will then be used as an input to the model of propagation throughout the limited zone of the patient's vasculature. Several parameters can be extracted from the three dimensional image, for example the centerline and diameter of the vessels, as well as the surface of the vessels.

In step S3 of selecting a second entry point, a second entry point, different from said first entry point, within said imaged vasculature, is selected along one of the segmented visible vessels. This second entry point is located along a secondary artery or even may be located along a smaller vessel. This second entry point is located deeper in the network of vessels than was located the first entry point, since a limited zone of patient's vasculature should be visualized which corresponds to a deeper sub-network of the ramifications of the vessels, preferably a sub-network encompassing complex bifurcations or arteriovenous malformation. This second entry point might be selected by the user analyzing a complex pathology, or automatically selected during a therapeutic procedure at a tool tip based on the external information that allows for monitoring and locating the tool, such as two dimensional X-ray images or an electro-magnetic tool tracking system.

In step S4 of simulating contrast propagation, contrast agent propagation is simulated, from selected second entry point, in a limited zone of said imaged vasculature. From this selected second entry point, propagation is simulated in the direction of blood flow, which may easily be known from the region of interest which is to be visualized. Indeed, if this region of interest is above the heart of the patient, the propagation within the arteries will be in the upper direction, from this selected second entry point. On the contrary, if this region of interest is below the heart of the patient, the propagation within the arteries will be in the lower direction, from this selected second entry point.

When using a model of contrast propagation, a contrast propagation from the second entry point inside the patient's vessel is simulated to help the three dimensional rendering of the vessel. As this work is done for a visualization purpose, it is indeed not necessary to have an accurate modeling of the contrast propagation. A very simple implementation that will simulate the propagation along the center line of the vessels will be sufficient. The geodesic distances from the second entry point of the contrast to the rest of the vessel tree are computed. The output is a three dimensional image of the geodesic distance. Assuming a constant velocity v, it can be assumed that at a time t, the vessel are filled up to a geodesic distance $d=v*t$ with concentration $c(d)$ made either constant or constant for a time window $\Delta T$ and then inversely proportional to distance d to simulate the dilution of the contrast within the blood stream with time.

Indeed, for embodiments of the invention, the preferred purpose is not to perfectly simulate the blood propagation in the patient's vasculature. This is more about automatically selecting the vessels which are rendered on the visualization workstation and ease the understanding of their architecture, especially in a region of interest, preferably corresponding to a complex bifurcation or an arteriovenous malformation.

In step S5 of visualizing a limited zone, the visualized limited zone only comprises some of said segmented visible vessels which had been identified thanks to at least part of patient's vasculature being previously imaged. This limited zone comprises at least some of said segmented visible of a locally complex network of vessels where the radiologist is manipulating a tool, or the feeding vessel(s) of an arteriovenous malformation which is there the region of interest to be visualized and analyzed by the radiologist. With the use of the model of contrast propagation, the propagation of the contrast inside the patient's vasculature is simulated with respect to time. The map of the vessels is shown according to the level of contrast inside the vasculature as a function of time. Thus, the vascular path may be given a constant intensity from the second entry point to all points at distance d=v*t further in the possible vascular paths originating in the second entry point, making this portion visible while all others are not. A set of images is computed for a set of N time points $\{t_i\}$ from $t_1$ to $t_N$ displaying for image i the vascular paths with constant intensity between the second entry point and points at distance $d_i=v*t_i$. The cinematic display of these images provides a dynamic rendering of the propagation. An alternative "bolus" propagation links the displayed intensity to the simulated concentration c(d) that is constant for a time window $\Delta T$ only, such that, when computing image $t_i$, the intensity decreases for a) all vessel points at distance d such that $d>v*\Delta T$ and b) for all vessel points at distance $d<v*\Delta T$ from the second entry but such that $|d-v*t_i|>\Delta T$. The visualization of this simple simulation of the propagation and dilution of a limited amount (bolus) of contrast agent will cinematically display the washing in and washing out of a limited zone of vessels.

An alternative, static, rendering method may use the 3-component decomposition of color into Hue, Saturation and Brightness (HSB). Constant saturation and brightness are given to all vessel points between the second entry point and end point $t_N$, while the Hue component is varied across time points to represent the propagation time. Customized color decompositions can further improve time representation. On FIG. 2, a static rendering will be described in more detail.

In step S6 of advancing, rewinding, stopping or looping through, the simulated contrast agent propagation can be stopped or advanced, by user, so as to graphically represent a vascular path of at least a segmented visible vessel of said limited zone. The number of times the user, for instance the radiologist, may go forward or backward along the vascular paths is not limited. Alternatively, a cinematic loop can be played. Therefore, the radiologist may visualize several times the vascular paths of interest so that the analysis performed may be more complete and more reliable. Again, this option makes easier visualization and associated interpretation of a complex bifurcation and of an arteriovenous malformation image by the radiologist. His or her assessment of the pathology or the needed treatment can be made safer that way. The user will have the possibility, at will, to stop, and or respectively rewind, advance or loop through, the contrast propagation within the vessels, to materialize on the displayed image, so to visualize less, or respectively more, of a vessel length and hence to follow a vascular path with great flexibility.

FIG. 2 shows schematically an example of a patient's vasculature image visualized by a three dimensional imaging method according to embodiments of the invention. Here, the three dimensional imaging of said simulated contrast agent propagation is a static graphic representation of said segmented visible vessels of said imaged limited zone with a static representation code, which is indeed a color code, as a function of propagation time from said second entry point.

A real patient's vasculature may be much more complicated and developed than the vasculature represented on FIG. 2, but the excessively simple vasculature represented on FIG. 2 allows for simply and clearly explaining the problem tackled by embodiments of the invention and the proposed solution to solve it.

The patient's vasculature represented on FIG. 2 comprises a main artery MA which splits into two secondary arteries SA1 and SA2. First secondary artery SA1 splits into vessels V1 to V13, whereas second secondary artery SA2 splits into vessels V20 to V30. It can be seen that vessels V6 to V13 of first secondary artery SA1 are superimposed on the image with vessels V20 to V30 of second secondary artery SA2.

Imaged vasculature is represented with different color coding corresponding to different propagation zones with respect to contrast propagation time. Contrast agent is injected at first entry point EP1, the injection direction being shown by the arrow. During a first propagation time interval, this injected contrast agent propagates in zone Z1; during a second propagation time interval, this injected contrast agent propagates in zone Z3; during a third propagation time, this injected contrast agent propagates in zone Z4. Limited zone Z2 is constituted by the reunion of zones Z3 and Z4. Main artery MA, first and second secondary arteries SA1 and SA2, vessels V1 to V13 and vessels V20 to V30, are then all selected.

In zone Z4, close to border with zone Z3, there is an AVM. This AVM is fed by the vessels V20 to V30 of second secondary artery SA2, but is not fed by the vessels V1 to V13 of first secondary artery SA1. However, the vessels V6 to V13 of first secondary artery SA1 are superimposed in the image of the vasculature with the vessels V20 to V30 of second secondary artery SA2.

Embodiments of the invention propose to separate the vessels V6 to V13 of first secondary artery SA1 from the vessels V20 to V30 of second secondary artery SA2. Therefore, a second entry point EP2 is selected by the user, usually a radiologist, for example at the border between zones Z1 and Z2, within second secondary artery SA2. Second entry point EP2 is selected downstream of first entry point EP1 so that zone Z2 is a limited zone of zone Z1.

No contrast agent is injected at second entry point EP2, but a simulation of contrast agent injection at second entry point EP2 is performed, the injection simulation direction being shown by the arrow. During a first propagation time interval, this simulated contrast agent propagates in zone Z3; during a second propagation time interval, this simulated contrast agent propagates in zone Z4. When this simulated propagation of contrast is visualized, only the vessels V20 to V30 fed by the second secondary artery SA2 are selected and displayed on screen, the vessels V1 to V13 of first secondary artery SA1 being neither selected nor displayed on screen. So, when the radiologist is looking at the AVM, he now sees, in the region of the AVM, only the vessels V20 to V30 of second secondary artery SA2 and no more the vessels V6 to V13 of first secondary artery SA1, which makes easier his or her understanding of the region of the AVM, by being able to look at only the feeding vessels of this AVM and by being able to more easily follow the vascular paths of interest with respect to this AVM. If the radiologist had simply zoomed in the region of the AVM instead, he would have looked at the entanglement of both groups of vessels V6 to V13 of first secondary artery SA1 and V20 to V30 of second secondary artery SA2, that would have rendered his or her analysis more difficult and more haphazard.

When the user or radiologist, wants to make use of the advance/stop function described in step S6 with respect to FIG. 1, he may alternatively contemplate zone Z3 with only vessels V20 to V30 of second secondary artery SA2 being represented (of course with part of second secondary artery SA2, but with no representation of vessels V6 to V13 of first secondary artery SA1) and zone Z4 with only vessels V20 to V30 of second secondary artery SA2 being represented (with no representation of vessels V6 to V13 of first secondary artery SA1). This again makes even easier his or her understanding of the region of the AVM, by being able to even more easily follow the vascular paths of interest with respect to this AVM.

The invention has been described with reference to preferred embodiments. However, many variations are possible within the scope of the invention.

The invention claimed is:

1. An imaging method for generating a three dimensional visualization of a limited zone of a patient vasculature, comprising:
   providing an imaging system comprising an imager to generate an image and a display;
   injecting a real contrast agent into the vasculature at a first entry point; and
   operating the imaging system to:
      image the vasculature to produce a set of two dimensional images, each image comprising real contrast agent propagation path information;
      generate a three dimensional visualization on the display of a propagation of the real contrast agent from the first entry point in said imaged vasculature from the set of two dimensional images;
      segment vessels of said imaged vasculature to confirm at least one vascular path;
      select a second entry point within said segmented imaged vasculature, the second entry point being different from the first entry point; and
      generate a three dimensional visualization on the display of a simulated propagation of contrast agent from the second entry point in a limited zone of said imaged vasculature to improve visualization of vessels in said limited zone.

2. The method of claim 1, wherein said second entry point is selected within one of said segmented visible vessels, wherein said imaged limited zone only comprises some of said segmented visible vessels.

3. The method of claim 1, wherein the method is performed by an interventional imaging system.

4. The method of claim 1, wherein said limited zone comprises at least some of said segmented visible vessels feeding a tumor or an arteriovenous malformation.

5. The method of claim 1, wherein said simulated contrast agent propagation can be stopped, rewound, advanced or looped through, by user, so as to graphically represent a vascular path of at least a segmented visible vessel of said limited zone.

6. The method of claim 1, wherein said three dimensional imaging of said simulated contrast agent propagation is a static graphic representation of said segmented visible vessels of said imaged limited zone with a static representation code as a function of propagation time from said second entry point.

7. The method of claim 1, wherein said three dimensional imaging of said simulated contrast agent propagation is a cinematic representation of said segmented visible vessels of said imaged limited zone, showing directly the propagation, from said second entry point, as a function of propagation time, of contrast along said segmented visible vessels of said limited zone.

8. The method of claim 1, wherein said first entry point is the entry point of main artery of said vasculature.

9. The method of claim 1, wherein second entry point is automatically selected as a tool tip position.

10. The method of claim 1, wherein each said segmented visible vessel is represented by only two parameters, its centerline and its diameter.

11. The method of claim 1, wherein said contrast agent propagation is simulated by progressively filling said segmented visible vessels of said limited zone up to a geodesic distance of $d=v*t$ from said second entry point, with v a constant velocity, with t the propagation time.

12. The method of claim 1, wherein said contrast agent propagation is simulated together with contrast dilution for a limited amount (bolus) of contrast allowing visualization for a time window $\Delta T$ only.

13. The method of claim 1, wherein said segmented visible vessels of said limited zone include vessels which diameter is less than 1 mm.

14. An interventional imaging system configured to perform the method of claim 1.

15. The method of claim 6, wherein the static representation code is a color code.

16. The method of claim 1, wherein said three dimensional visualization of real contrast agent propagation from said first entry point is computed from at least 100 two dimensional images each including real contrast agent propagation information.

* * * * *